United States Patent [19]
Heiler et al.

[11] Patent Number: 5,603,897
[45] Date of Patent: Feb. 18, 1997

[54] METHOD FOR INDICATING NEUTRALIZATION OF CONTACT LENS DISINFECTING SOLUTIONS

[75] Inventors: David J. Heiler, Avon; Matthew S. Jonasse, Sodus; David A. Marsh, Rochester; Jill S. Rogalskyj, Livonia, all of N.Y.

[73] Assignee: Bausch & Lomb Incorporated, Rochester, N.Y.

[21] Appl. No.: 268,473

[22] Filed: Jun. 30, 1994

[51] Int. Cl.$^6$ ............................... A61L 2/16; A61L 2/18
[52] U.S. Cl. .................. 422/30; 422/28; 422/29; 422/119; 424/78.04; 424/672; 436/93; 436/94; 436/96; 514/839; 514/840; 514/912
[58] Field of Search ............... 424/78.04, 672; 422/28, 29, 119, 30; 436/93, 94, 96; 514/839, 840, 912

[56] References Cited

U.S. PATENT DOCUMENTS

| | | | |
|---|---|---|---|
| 3,911,107 | 10/1975 | Krezanoski | 424/78 |
| 4,031,209 | 6/1977 | Krezanoski | 424/150 |
| 4,234,313 | 11/1980 | Faulkner | 23/230 |
| 4,863,627 | 9/1989 | Davies et al. | 252/95 |
| 4,976,969 | 12/1990 | Plamondon | 424/672 |
| 5,531,963 | 7/1996 | Powell | 422/30 |

FOREIGN PATENT DOCUMENTS

| | | |
|---|---|---|
| WO92/04922 | 4/1992 | WIPO . |
| WO92/04921 | 4/1992 | WIPO . |

OTHER PUBLICATIONS

Advanced Inorganic Chemistry, 5th ed., Cotton and Wilkinson (Wiley and Sons, New York) p. 548 (1988).

*Primary Examiner*—Richard L. Raymond
*Attorney, Agent, or Firm*—Edward W. Black; Chris P. Konkol

[57] ABSTRACT

A method of treating contact lenses comprising the use of an iodine-chromophore to indicate neutralization of oxidative disinfectants.

22 Claims, No Drawings

METHOD FOR INDICATING NEUTRALIZATION OF CONTACT LENS DISINFECTING SOLUTIONS

BACKGROUND OF THE INVENTION

This application relates to methods for treating contact lenses and particularly relates to methods for disinfecting lenses with oxidative disinfectants.

Through ordinary use, contact lenses accumulate dirt, proteinaceous matter, microorganisms and the like, all of which can adversely affect both the usefulness of the lens and the health of the eye. Therefore, contact lenses must be cleaned and disinfected regularly.

It is known that certain compounds will readily clean and/or disinfect contact lenses. For example, solutions of peroxides, hypochlorites, persulfates and other oxidative solutions are known to clean and disinfect contact lenses. However, disinfecting soft contact lenses, especially hydrogel lenses, using such oxidative chemical agents presents a particular problem in that the lenses can absorb, into the polymeric matrix, the agents from the disinfecting solutions in which they soak. Such oxidative agents, if left in the lens, will irritate the eye of the wearer if even a small amount of the agent remains on the lens when it is inserted in the eye.

Disinfecting systems are known where a neutralizing agent acts on the oxidative agents in the contact lens solution so that, after the lens has been disinfected, the active agents are neutralized. See U.S. Pat. Nos. 3,911,107 and 4,031,109. After such neutralization, the lens, usually after rinsing, can be worn without danger of irritation. Many of these systems are slow, designed to take many hours, or be an "overnight" regimen.

It is difficult to be certain when the oxidative reagent has been effectively neutralized and the lens is safe to wear. Time-oriented regimens, whereby the neutralization takes a fixed amount of time before the lenses may be safely inserted in the eye, rely on strict compliance with the regimen by the lens wearer. Consumers more easily comply with a lens care format if it is rapid and easy to administer.

Various indicator systems have been incorporated into contact lens disinfection regimens. PCT Application No. PCT/US91/06526 discloses the use of complex redox polymers having repeating bypyridinium units as indicators for determining the presence of an oxidative disinfectant in a contact lens solution. U.S. Pat. No. 4,863,627 discloses the use of known redox indicators such as methylene blue, and triphenylmethane dyes in a contact lens solution regimen. However, most known redox indicators do not produce a rapid color change (i.e. within 5 minutes) at neutral pH when the solution is cold or at room temperature.

SUMMARY OF THE INVENTION

The present invention provides a method of treating a contact lens which comprises contacting the lens with an oxidative disinfectant and neutralizing the disinfectant with a reducing solution, the improvement which comprises using an iodine-chromophore to indicate when neutralization is complete.

The colored iodine-chromophore indicator will disappear after the disinfectant has been neutralized, allowing the user to accurately know when the contact lenses are safe to wear. The iodine-chromophore oxidative indicators of the present invention are useful at room temperatures and neutral pH. Their use facilitates compliance with a contact lens disinfection/neutralization regimen which is safe, rapid and easy to perform.

DETAILED DESCRIPTION OF THE INVENTION

The iodine chromophore of the present invention is any color producing complex comprised of iodine or iodine derivative ions associated with an amylose-containing compound or complex. "Chromophore" for the purpose of this application refers to any color producing compound. The iodine chromophore may be provided to the disinfecting solution in a solid or liquid form. Particularly preferred is the incorporation of the iodine-chromophore in a tablet which also contains the oxidative disinfectant.

An amylose is understood to be the linear, helical component of starch. It is believed that the known iodine-starch complex indicator system is the result of the iodine molecules becoming closely associated in a linear array and "held" within the helical structure of the amylose. Any amylose-containing compound which associates with iodine to create a chromophore may be used in this invention. Preferred amylose-containing compositions for use in the iodine chromophore are starch, and hydrolyzed starches such as dextrins, with maltodextrin being particularly preferred.

The amylose-containing compounds and the iodine must be present in the prepared iodine-chromophore in an amount such that the disinfecting solution will be perceptibly colored when an oxidative agent is present. When neutralization of the oxidative disinfectant is complete, the color will disappear, indicating to the lens wearer that the lens is ready to be removed from the disinfecting solution, rinsed, and safe for use.

Since contact lens disinfection is preferably conducted at neutral pH, the amylose-containing component of the iodine-chromophore is desirably soluble in room temperature aqueous solution and neutral pH. When the iodine-starch complex is desirable, it has now been discovered that starch solubility at neutral pH and room temperature is achievable by first adding polyvinyl pyrrolidone to the commercially available soluble starch solution, and then extracting the solid starch via reduced pressure (e.g. rotoevaporation or lyophilization). The resulting fluffy white powder was combined with an iodine source, such as polyvinyl pyrrolidone-iodine to create a tablet that was highly soluble in cool or room temperature aqueous solution, and which gave a vivid blue/purple color in the presence of oxidative reagents at neutral pH.

Iodine may be provided to the chromophore complex of this invention in any suitable form (i.e. $I_2$, $I^-$, $I_3^-$, etc.). The exact mechanism by which iodine, iodide or its derivative ions associate within the helical amylose molecule is not fully understood. Iodine as referred to herein will refer to all molecular forms of iodine which may associate with an amylose molecule to create a chromophore. The iodine is most preferably provided to the disinfecting reaction in tablet form to produce concentrations in solution of from about 5 ppm to about 100 ppm, more preferably from about 10 ppm to about 50 ppm, and most preferably from about 20 ppm to about 30 ppm.

Providing carrier complexes for the iodine, or "iodophors", is known to improve the solubility of iodine in aqueous solutions. Any known iodophor may be suitable for use in the present invention. The preferred iodophor selected for use in the present method must provide a sufficient concentration of iodine to rapidly associate with the amylose provided to the disinfecting solution.

Particularly useful carriers which associate with iodine to create iodophors include a variety of high molecular weight polymeric materials such as starch and various synthetic polymers. Specific examples of suitable polymeric materials include polyvinyl pyrrolidone and copolymers thereof (such as vinyl acetate polyvinyl pyrrolidone), polyvinyl oxizolidone, caprolactam, polyvinyl alcohol, ethylene and propylene oxide condensates having alcohol, amide and phenol groups, with polyvinyl pyrrolidone being the most preferred. In the preferred embodiment, an iodophor tablet created to give a concentration of about 200 ppm polyvinyl pyrrolidone-iodine will provide about 20 ppm active iodine. The amounts of iodophor required to yield a desired amount of active iodine will vary slightly.

The oxidizing disinfectants may be any compounds which disinfect through oxidative action, which can be neutralized through reduction, and which can be detected with a redox indicator. The oxidative disinfectants may be added to an aqeous solution as a solid (e.g. tablet, powder, etc.) or may be added as a liquid. Preferred examples of oxidative disinfectants include, peroxides, persulfates, hypochlorites, percarbonates, urea peroxides, permanganates, ozones, chloramines, and electron deficient quinones, with peroxides being most preferred.

The amount of disinfectant provided must be sufficient to adequately disinfect a contact lens. In one preferred embodiment, the use of a peroxide at a concentration range of from about 0.5 weight % to about 5.0 weight % is preferred, with from about 2.5 weight % to about 3.5 weight % being most preferred.

After lens disinfection is complete, a reducing agent is added to the colored disinfecting solution to neutralize the oxidative disinfectant. The reducing agent selected for use in the method of the present invention may be any compound having the appropriate redox potential to neutralize the oxidative disinfectant selected. Examples of preferred reducing compounds include alkali metals of thiosulfates, sulfites, thioglycerol, formates, pyruvic acid and salts of pyruvic acid, N-acetylcysteine,ene-diol compounds, e.g. ascorbic acid compounds, reductive acid compounds, isoascorbic compounds, glyoxylic acid compounds, dihydroxymaleic acid compounds, dihydroxyfumaric acid compounds, and mixtures thereof. Particularly preferred are ascorbic acid and derivatives thereof and the thiosulfates and derivatives thereof, with the sodium thiosulfate being most preferred.

While the reducing agent may be provided in any physical state, it is preferably a liquid. The concentration of the reducing agent required for neutralization of the disinfectant is determined by the concentration of disinfectant in the disinfecting solution, as is apparent to one skilled in the art. In the preferred embodiment of this invention, where sodium thiosulfate is the reducing agent, the concentration of the thiosulfate in aqueous solution is preferably in the range from about 0.003 weight % to about 0.3 weight %, and more preferably from about 0.01 weight % to about 0.3 weight %.

As the lens disinfection takes place, and so long as any oxidative disinfectant is present in the disinfecting solution, the solution will be colored. The hue is dependent upon the relative concentration and type of amylose used and upon the available concentration of iodine in solution. The color lightens as the reducing agent neutralizes the oxidative disinfectant up to the point when the solution is colorless, indicating that the disinfectant has been neutralized and the lenses are safe to wear.

It is understood that an optional neutralizing rinse, or rub and rinse of the lens after removing the lens from the disinfecting/neutralized solution may result in greater comfort and be incorporated into the protocol of the method of the present invention. It is further understood that the lenses may also be cleaned during the disinfection phase, or that separate cleaners may be added such that cleaning and disinfection occur together.

The indicators used in the disinfecting method of the present invention are contemplated for use with any type of hard or soft contact lens. However, it is believed that the oxidative disinfecting system of the present invention would be particularly useful for the disinfection of soft hydrogel contact lenses which are thought to possibly absorb some of the oxidative disinfectants.

Hydrogels are understood to be hydrophilic polymers that absorb water to an equilibrium value and are insoluble in water due to the presence of a three-dimensional network. Hydrogels are generally formed of a copolymer of at least one hydrophilic monomer and a crosslinking monomer. The swollen equilibrated state results from a balance between the osmostic driving forces that cause the water to enter the hydrophilic polymer and the forces exerted by the polymer chains in resisting expansion.

If the iodine associated with the amylose in the iodine-chromophore is provided in sufficient concentration, it may behave as a disinfectant which may further enhance disinfection of the lenses. Since the active iodine is itself an oxidative agent, it will also be neutralized along with the oxidative disinfectant upon exposure to the reducing solution.

The invention is more fully described in the following examples which are illustrative, but not considered limiting of the invention.

EXAMPLE 1

Starch Preparation

Attempts were made to extract starch from a commercially available soluble starch solution followed by combination with an iodine source, such as KI. However, tablets made from this combination were not sufficiently soluble when reintroduced to cool or room temperature water (neutral pH) and further provided no color as a result of the starch-iodine complex in the presence of oxidative reagents.

When starch is the desired component of the iodine-chromophor oxidative indicator, the following procedure is used to solubilize the starch into a form which can be tableted and go into solution.

Two grams of polyvinylpyrrolidone (PVP K-15, GAF, MW=15,000), was dissolved into 100 ml of commercially available Starch Indicator Solution (Fisher) after 5 minutes of stirring at room temperature. The mixture was placed into a lyophilization flask and frozen using a mixture of dry ice and acetone. The frozen mixture was then "freeze-dried" in an Edwards lyophilizer overnight (18 hours). The resulting compound after freeze-drying was fluffy and easy to use in compounding the disinfecting tablet.

Previous attempts to solubilize starch recovered from the stock Starch Indicator Solution (Fisher) were unsuccessful as the starch powder was not sufficiently soluble in the disinfecting solutions at room temperature and neutral pH. It is believed that the PVP K-15 suspends the starch, preventing aggregation of starch and improving solubility.

EXAMPLE 2

Liquid Starch Iodine Indicator

Polyvinylpyrrolidone-hypochlorite was synthesized by mixing 0.25 weight % polyvinyl pyrrolidone (PVP K-25

GAF, MW=25,000) with 0.025 weight % sodium hypochlorite into 90 mls of purified water. The solution remained at room temperature for four days, followed by lyophilization in an Edwards lyophilizer to yield a white powder. The following solution was prepared in 90 mls of water:

0.275 weight %—PVP-hypochlorite 0.05 weight %—dibasic sodium phosphate 4.0 weight %—Starch Indicator Solution (Fisher)

0.06 weight %—Potassium Iodide

The solution is brought to a total volume of 100 mls. The pH was adjusted to 7.2 using dilute HCl. The formulation produced a blue solution having an active iodine concentration of about 25 ppm.

EXAMPLE 3

Preparation of Starch-Iodine Indicating Tablet (70 ppm Active Iodine)

A starch-iodine indicating tablet designed to be dissolved in 6 mls of reducing solution was prepared having the following formulation:

4.2 mg PVP-$I_2$ (70 ppm active iodine) USP Grade (BASF)

3.6 mg PVP-Starch (made according to the protocol of Example 1)

50 mg Sodium Chloride 20 mg Tartaric Acid 22.5 mg Sodium Carbonate

Prior to compounding, tartaric acid was milled and passed through an 80 mesh sieve and dried 24 hours at 70 degrees C. Sodium carbonate was also passed through an 80 mesh sieve and dried for 24 hours at 70 degrees C. Sodium chloride was also dried at 70 degrees for 24 hours. The components were combined and the mixture passed through a 30 mesh sieve. The remaining larger particles were crushed with a pestle-mortar. The combined mixture was V-blended for 1 hour and then tableted with a 6 mm punch for a 100 mg weight.

EXAMPLE 4

Preparation of Maltodextrin-Iodine Indicating Tablet (70 ppm Active Iodine)

A maltodextrin-iodine indicating tablet designed to be dissolved in 6 mls of reducing solution was prepared having the following formulation:

4.2 mg or 700 ppm of PVP-Iodine (70 ppm active iodine) USP grade (BASF);

3.6 mg Maltodextrin (Maltrin$^R$ M040, GPC, Muscatine, Iowa)

50 mg Sodium Chloride 20 mg Tartaric Acid 22.5 mg Sodium Carbonate

Prior to compounding, tartaric acid was milled and passed through an 80 mesh sieve and dried 24 hours at 70 degrees C. Sodium carbonate was also passed through an 80 mesh sieve and dried for 24 hours at 70 degrees C. Sodium chloride was also dried at 70 degrees for 24 hours. The components were combined and the mixture passed through a 30 mesh sieve. The remaining larger particles were crushed with a pestle-mortar. The combined mixture was V-blended for 1 hour and then tableted with a 6 mm punch for a 100 mg weight.

Many other modifications and variations of the present invention are possible and will be apparent to the skilled practitioner in the field in light of the teachings herein. It is therefore understood that, within the scope of the claims, the present invention can be practiced other than as herein specifically described.

We claim:

1. In a method of treating a contact lens which comprises contacting the lens with an oxidative disinfectant and neutralizing the disinfectant with a reducing solution, the improvement which comprises using a water soluble iodine-chromophore to indicate when neutralization is complete.

2. The method of claim 1 wherein the iodine-chromophore comprises an amylose.

3. The method of claim 2 wherein the amylose is selected from the group consisting of amylose-containing starch and dextrins.

4. The method of claim 2 wherein the amylose is maltodextrin.

5. The method of claim 1 wherein the iodine-chromophore comprises an iodine-starch complex.

6. The method of claim 5 wherein the starch of the iodine-starch complex is a solubilized starch.

7. The method of claim 6 wherein the solubilized starch comprises polyvinylpyrrolidone.

8. The method of claim 1 wherein the iodine of the iodine-chromophore is provided by an iodine-generating compound selected from the group consisting of potassium iodide and polyvinylpyrrolidone-iodine.

9. The method of claim 1 wherein the iodine of the iodine-chromophore is provided by polyvinylpyrrolidone-iodine.

10. The method of claim 1 wherein iodine is present in a concentration of from about 5 ppm to about 100 ppm.

11. The method of claim 1 wherein the iodine is present in a concentration of from about 10ppm to about 50 ppm.

12. The method of claim 1 wherein the iodine is present in a concentration of from about 20 ppm to about 30 ppm.

13. The method of claim 1 wherein the iodine-chromophore is provided in a solid form.

14. The method of claim 1 wherein the iodine-chromophore is provided in a tablet form.

15. The method of claim 1 wherein the iodine-chromophore is provided in liquid form.

16. The method of claim 1 wherein the oxidative disinfectant is selected from the group consisting of peroxides, persulfates, hypochlorites, percarbonates, urea peroxides, permanganates, ozones, chloramines, and electron deficient quinones.

17. The method of claim 1 wherein the oxidative disinfectant is a peroxide.

18. The method of claim 1 wherein the oxidizing disinfectant and the iodine-chromophore are together in one tablet provided to a solution to form a colored disinfecting solution.

19. The method of claim 1 wherein the reducing solution comprises a reducing agent selected from the group consisting of ascorbic acid, ascorbic acid derivatives, and thiosulfate-containing compositions.

20. The method of claim 1 wherein the reducing solution comprises a thiosulfate-containing composition.

21. The method of claim 1 wherein the reducing solution comprises sodium thiosulfate.

22. The method of claim 1 wherein the contact lens is a hydrogel contact lens.

\* \* \* \* \*